United States Patent [19]
Bittner et al.

[11] Patent Number: 5,931,847
[45] Date of Patent: *Aug. 3, 1999

[54] SURGICAL CUTTING INSTRUMENT WITH IMPROVED CUTTING EDGE

[75] Inventors: John R. Bittner, Loveland; Peter Lau, Cincinnati; David H. Ruder, Mason; W. G. Bowser, Maineville, all of Ohio

[73] Assignee: Ethicon Endo-Surgery, Inc., Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/775,537

[22] Filed: Jan. 9, 1997

[51] Int. Cl.$^6$ ............. A61B 17/32; A61B 17/04
[52] U.S. Cl. ........................ 606/167; 227/180.1
[58] Field of Search .................. 606/119, 120, 606/139, 142, 143, 151, 157, 167, 176, 177, 185, 219–221; 227/19, 178.1, 176.1, 180.1

[56] References Cited

U.S. PATENT DOCUMENTS

| | | |
|---|---|---|
| 3,636,943 | 1/1972 | Balamuth . |
| 3,888,004 | 6/1975 | Coleman .................................. 30/272 |
| 4,188,952 | 2/1980 | Loschilov et al. . |
| 5,064,411 | 11/1991 | Gordon, III .............................. 604/48 |
| 5,188,102 | 2/1993 | Idemoto et al. . |
| 5,217,477 | 6/1993 | Lager ...................................... 606/167 |
| 5,261,922 | 11/1993 | Hood ....................................... 606/169 |
| 5,263,629 | 11/1993 | Trumbull et al. ....................... 227/181 |
| 5,282,816 | 2/1994 | Miller et al. ............................ 606/167 |
| 5,292,330 | 3/1994 | Shutt ....................................... 606/170 |
| 5,314,417 | 5/1994 | Stephens et al. ....................... 604/264 |
| 5,342,380 | 8/1994 | Hood ....................................... 606/169 |
| 5,397,324 | 3/1995 | Carroll et al. .......................... 606/139 |
| 5,415,334 | 5/1995 | Williamson et al. .................. 227/178 |
| 5,443,475 | 8/1995 | Auerbach et al. ...................... 606/170 |
| 5,485,947 | 1/1996 | Olson et al. .......................... 227/176.1 |
| 5,542,594 | 8/1996 | McKean et al. ...................... 227/178.1 |
| 5,549,628 | 8/1996 | Cooper et al. .......................... 606/220 |
| 5,554,164 | 9/1996 | Wilson et al. .......................... 606/167 |

Primary Examiner—Glenn K. Dawson
Attorney, Agent, or Firm—Louis J. Capezzuto

[57] ABSTRACT

A surgical tissue fastening device for fastening and transecting tissue includes a handle having a cartridge assembly connected the handle. The cartridge assembly includes a cartridge containing a plurality of surgical fasteners. An anvil assembly is connected to the handle and includes an anvil surface that is positionable adjacent the cartridge. The anvil surface receives and forms the fasteners ejected from the cartridge upon firing of the instrument. Tissue that is desired to be fastened and transected is placed between the anvil and the cartridge. The instrument also includes a knife blade which is movable between the cartridge and the anvil for cutting the tissue. The knife blade has a knife edge having a plurality of pairs of cutting tips for piercing the tissue and a notch located between each pair of cutting tips for capturing foreign objects, such as staples, in the notch. An actuator assembly is operatively connected to the cartridge assembly and the knife blade for ejecting the fasteners from the cartridge to the anvil surface and for advancing the knife blade through the tissue for transecting the tissue between the cartridge and the anvil.

2 Claims, 6 Drawing Sheets

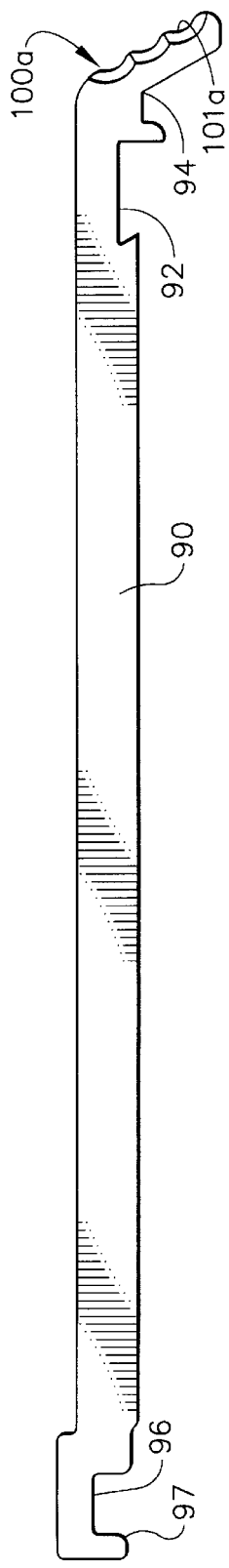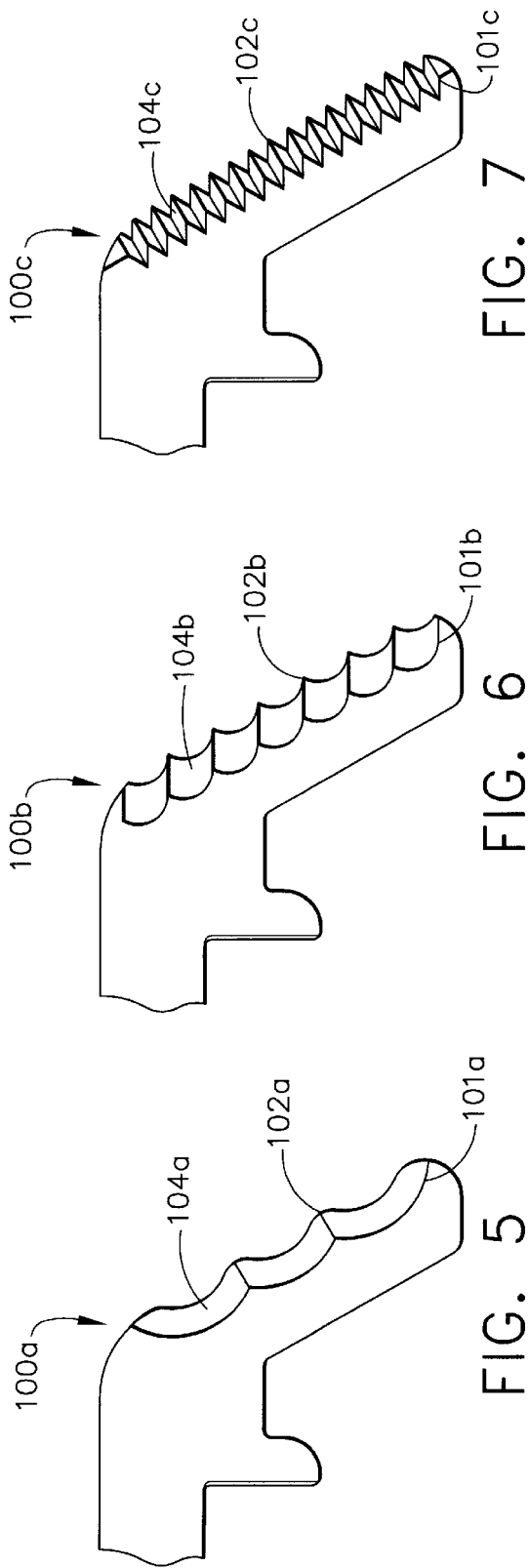

SURGICAL CUTTING INSTRUMENT WITH IMPROVED CUTTING EDGE

FIELD AND BACKGROUND OF THE INVENTION

The present invention relates, in general, to surgery and, in particular, to a new and useful surgical transection or cutting device for fastening and transecting tissue.

During many surgical procedures, it is common to use a tissue fastening device, such as a linear cutter, for stapling and transecting tissue in order to resect the tissue and achieve hemostasis by placing a plurality of laterally spaced rows of staples on opposite sides of a tissue cut or tissue transection line. The tissue transection line is placed in the tissue by advancing a cutting blade through the tissue simultaneously with the firing of the staples. For those surgical procedures which require the transection of tissue with a linear cutter, it is important that the cutting blade of the linear cutter have a quality cutting edge for penetrating and cutting the various types of tissue that are normally encountered during a procedure. Moreover, it is also important to have a cutting blade with an edge that can cut through varying thicknesses of tissue as well as have the ability to cut through other structures which may be encountered while cutting the tissue. Thus, when using a linear cutter, it is of great importance that the cutting blade remain sharp and resist dulling over repeated firings of the device.

As mentioned above, there are various surgical procedures which require a surgical transection or cutting device, such as a linear cutter. Some of these procedures not only utilize a linear cutter but also include a buttress material to be used in conjunction with the linear cutter. A buttress material, sometimes referred to as a pledget material, is placed between the staples and the tissue in an effort to achieve better hemostasis and/or pneumostasis. U.S. Pat. No. 5,263,629 (Trumbull et al.), U.S. Pat. No. 5,397,324 (Carroll et al.), U.S. Pat. No. 5,542,549 (McKean et al.) and U.S. Pat. No. 5,549,628 (Cooper et al.) disclose typical surgical instruments used in conjunction with buttress material for many different surgical procedures.

A lung volume reduction procedure is one of these procedures in which a section of lung tissue is removed with a linear cutter. During a lung volume reduction procedure, it is common to resect portions of a patients lung in order to remove diseased lung tissue from healthy lung tissue. This procedure usually requires multiple firings from the linear cutter or other types of surgical transection instruments. As a result of these multiple firings, it is a common occurrence for the staple lines which have been placed in the lung tissue to be crossed with the newly fired lines. The crossing of staple lines occurs in an effort to resect only those sections of diseased lung tissue that are necessary in an effort to preserve the integrity of the remaining lung tissue. Accordingly, when crossing staple lines, the cutting blade of the linear cutter often encounters the staples in the tissue which have been previously placed from previous firings. When encountering a previously placed staple, the surgeon often encounters difficulty in completing the firing stroke due to increased forces to fire as a result of the staple being located directly in the path of the cutting blade. Moreover, upon encountering a previously placed staple or any other obstruction located in the cutting path of the cutting blade, the cutting blade is usually dulled because the staple will engage the cutting edge of the cutting blade and will travel along the length of the edge. As a result of the staple dulling the blade edge, the surgeon will find it extremely difficult to transect tissue on subsequent firings for those linear cutters which have cutting blades prescribed for multiple firings.

For surgical linear cutter devices, such as those mentioned above, the cutting edge of the cutting blade has a linear and uniform configuration. However, one known prior art reference, U.S. Pat. No. 5,554,164 (Wilson et al.), discloses a linear cutter device having a non-linear cutting edge for preventing uncut tissue, otherwise known as a wisp, from sliding between the cutting blade and the upper finger of the linear cutter. The blade edge design has a single tip at opposite ends of the blade edge which is directed to preventing the wisping of the tissue. Although this non-linear blade configuration may avoid the formation of wisps within the surgical cutter, one major drawback to the blade edge design is that it is ineffective in preventing dulling of the cutting edge upon encountering an object, such as a staple, located in the cutting path of the cutting blade. Accordingly, upon encountering a staple in the cutting path, the staple is not prevented from moving along a substantial portion of the blade edge. Thus, a substantial portion of the cutting edge will be dulled and completion of the cutting stroke will be extremely difficult. Furthermore, since the cutting blade is disposed of along with the cartridge after the initial firing, subsequent usages of the dulled edge is not an issue.

Presently, one known way which is utilized to provide a quality cutting edge on a surgical linear cutter is to utilize a disposable cartridge which includes a cutting blade such that after each firing of the linear cutter, the expended cartridge and the used blade are disposed of and a new cartridge containing a new cutting blade is loaded in the linear cutter and utilized in the next firing of the instrument. A major drawback to this type of cartridge design is that there is a substantial cost associated with a cartridge that includes a one time use disposable cutting blade that is disposed of along with the spent cartridge upon one firing of the linear cutter.

Presently, there is no known surgical transection device or tissue fastening device, such as a linear cutter, that can ensure an effective cutting edge upon encountering a previously fired staple or other object located in tissue along its initial cutting stroke as well as subsequent usages.

SUMMARY OF THE INVENTION

The present invention is a surgical transection device, such as a linear cutter, which is used to fasten and transect tissue. The surgical transection device according to the present invention comprises a handle and a cartridge assembly connected to the handle. The cartridge assembly includes a cartridge containing a plurality of surgical fasteners. An anvil assembly is connected to the handle and includes an anvil surface which is positionable adjacent the cartridge. The anvil surface receives and forms fasteners which are ejected from the cartridge after tissue has been placed between the anvil and the cartridge. A cutting blade is movably positioned between the cartridge and the anvil surface for cutting the tissue. The cutting blade has a cutting edge which comprises a plurality of cutting tips defining adjacent pairs of cutting tips and a notch interposed between each pair of cutting tips. An actuator assembly is operatively connected to the cartridge assembly and the cutting blade for ejecting the fasteners from the cartridge to the anvil surface while advancing the cutting blade for transecting the tissue.

It is an object of the present invention to provide a surgical tissue fastening and transection device that can effectively fasten and transect tissue even after encountering an object, such as a staple, located along the cutting path of the device.

It is another object of the present invention to provide a surgical tissue fastening and transection device that has a cutting element which is capable of completing multiple transections even after encountering an object such as a staple.

It is another object of the present invention to provide a surgical tissue fastening and transection device that has a cutting element which can maintain a sharp cutting edge even after encountering an object such as a staple.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 4 is a side elevational view of one embodiment of a blade used in the device of FIGS. 3A, 3B and 3C;

FIG. 5 is a view of the distal or working end of the blade of FIG. 4 shown in side elevation view;

FIG. 6 is an alternate embodiment of the distal or working end of the blade of FIG. 4 shown in side elevation view; and FIG. 7 is another alternate embodiment of the distal or working end of the blade of FIG. 4 shown in side elevation view.

DESCRIPTION OF THE PREFERRED EMBODIMENTS

Figure 1:
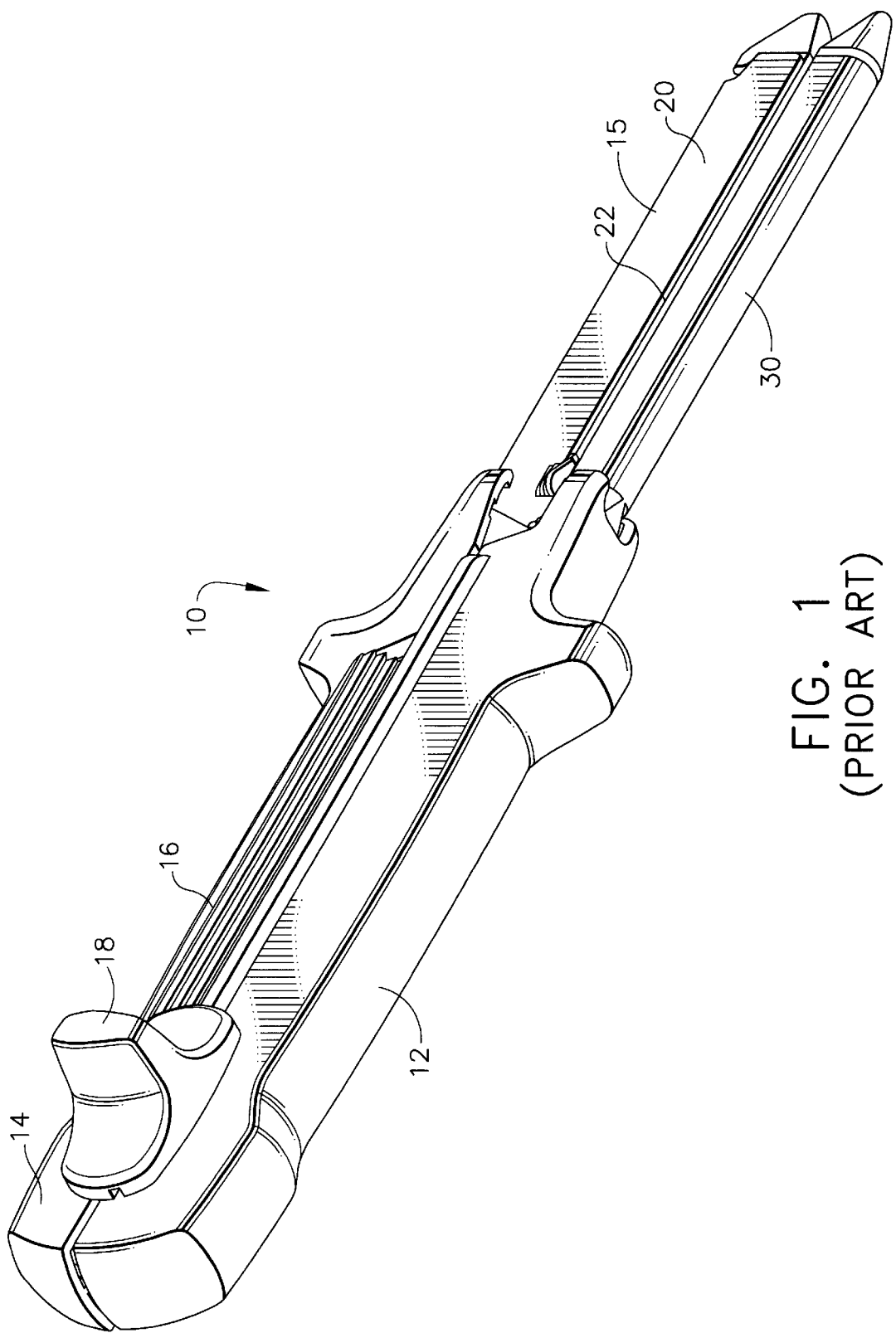
FIG. 1 is a perspective view of a surgical tissue fastening and transection device.

Referring to FIG. 1, there is shown a typical surgical tissue fastening and transecting device or stapling/cutting device (hereinafter "cutter"), generally designated 10, and generally of the type disclosed in U.S. Pat. No. 5,263,629 (Trumbull et al.); U.S. Pat. No. 5,415,334 (Williamson et al.) and U.S. Pat. No. 5,485,947 (Olson et al.); and U.S. patent application Ser. No. 08/232,906 assigned to Ethicon Endo-Surgery, Inc., the disclosure of which patents and application are incorporated herein by reference for a more complete discussion of certain structural details of the device.

Figure 2:
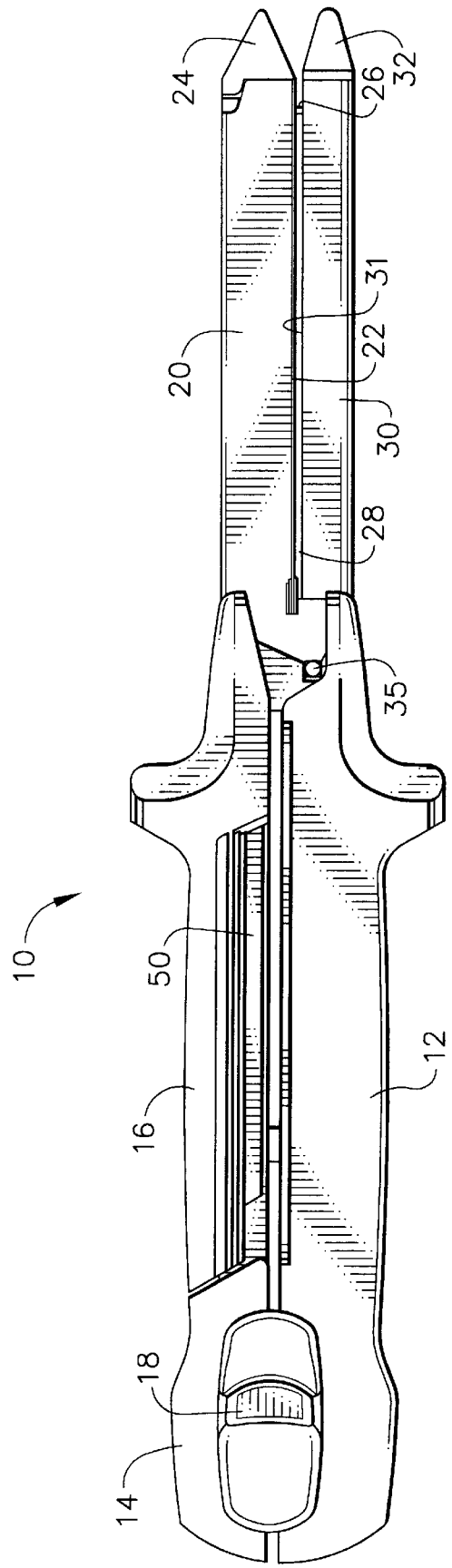
FIG. 2 is a side elevational view of the device of FIG. 1.

The cutter 10 is directed to fastening and transecting tissue and can be either a disposable device indicated for use on a single patient, e.g. a device for single patient use only or a reusable device for use on multiple patients. As best shown in FIGS. 1 and 2, the cutter 10 includes a handle comprising an anvil shroud 12 covering a proximal end of an anvil assembly 30, a cartridge channel shroud 14 covering a proximal end of a cartridge channel assembly 15 and a hook latch shroud 16 covering a hook latch 50. The cartridge channel shroud 14 and the hook latch shroud 16 are positioned opposite the anvil shroud 12.

Figure 3A:
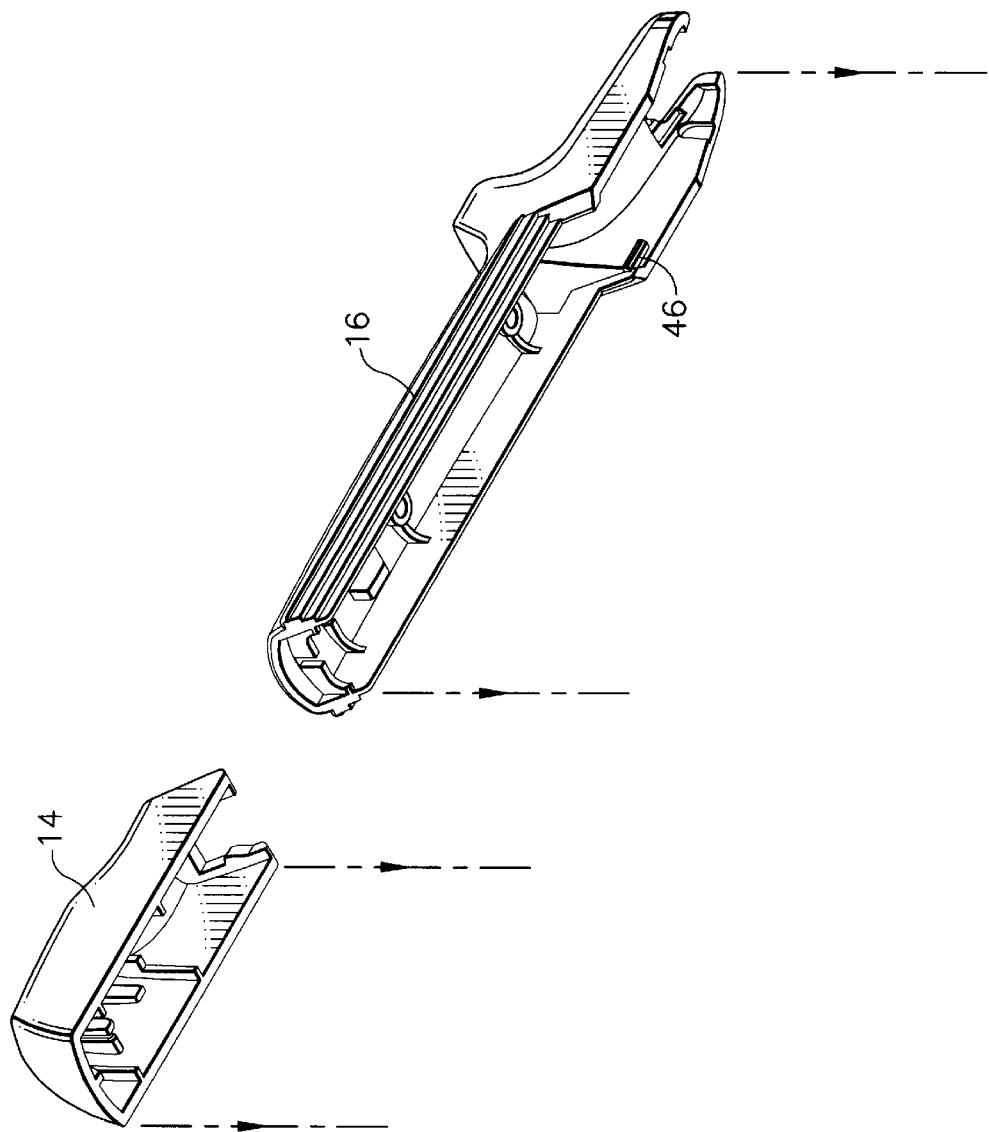
FIGS. 3A, 3B and 3C are an exploded perspective view of the device of FIGS. 1 and 2 showing parts in an orientation prior to assembly.
Figure 3B:
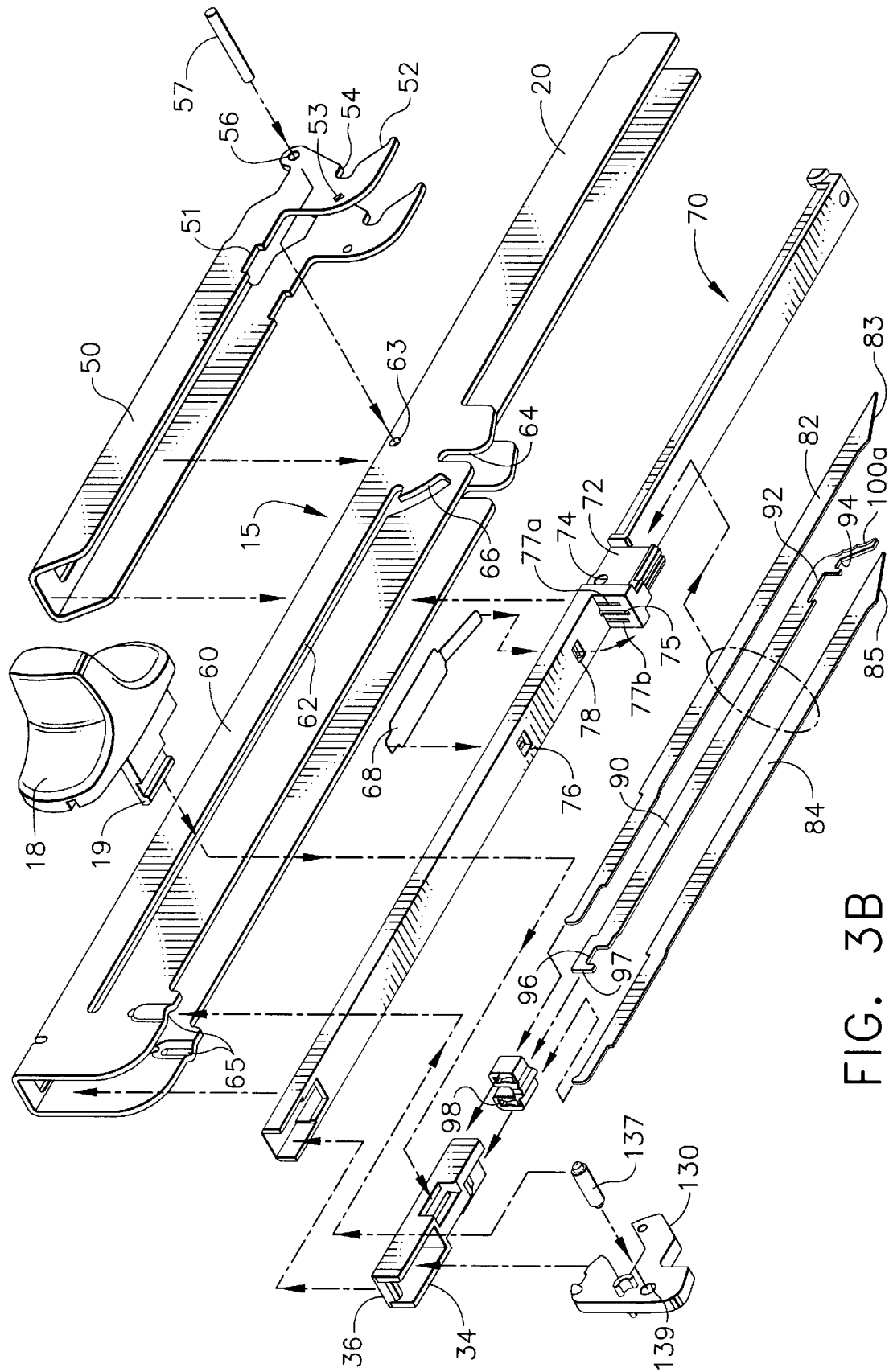
Figure 3C:
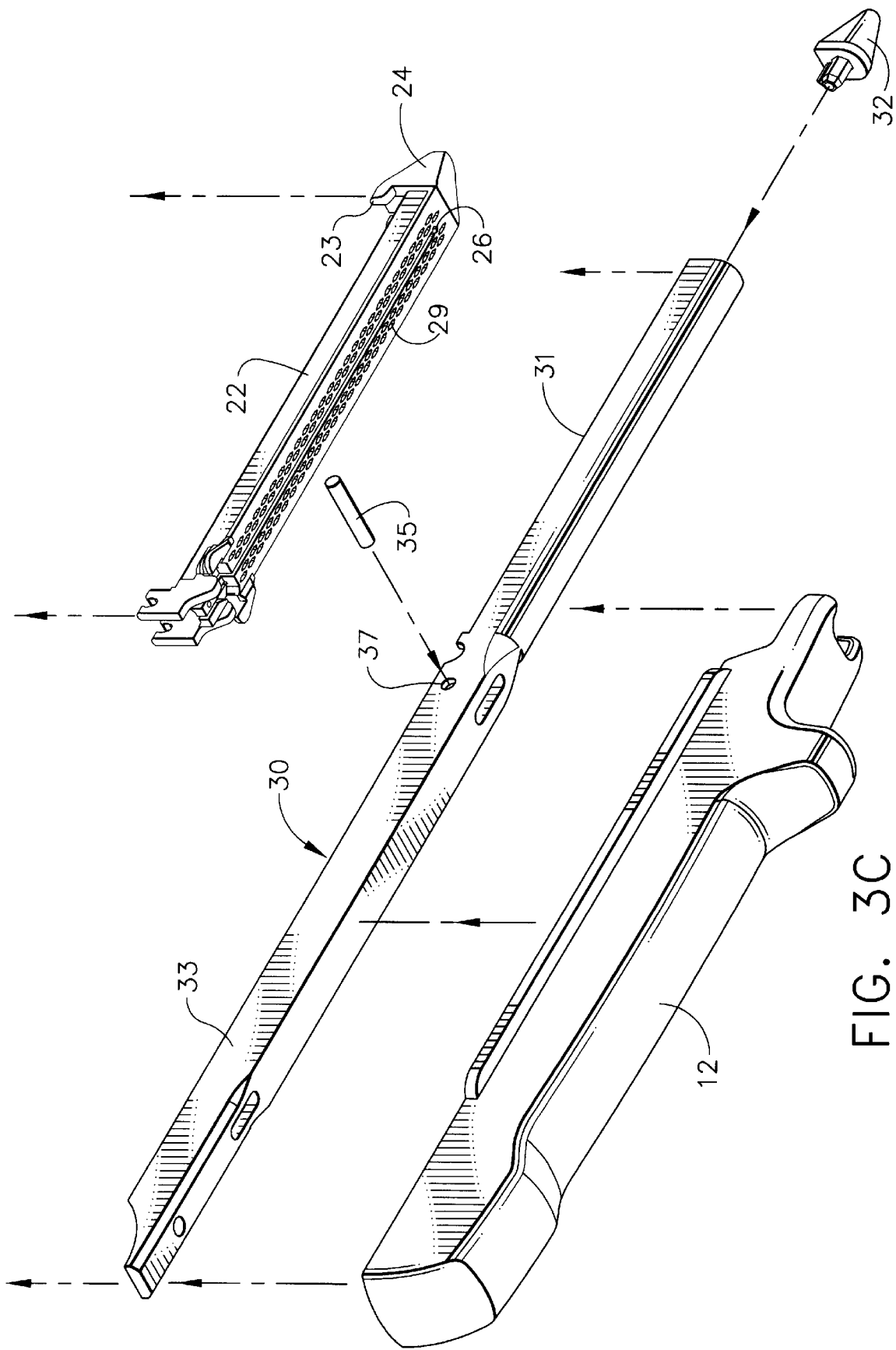

As shown in FIG. 3B, at the distal end of the cartridge channel assembly 15, opposite the cartridge channel shroud 14, the cartridge channel assembly 15 has a cartridge channel 20 for receiving a disposable staple cartridge 22 (illustrated in FIG. 3C). Attachment cleats 23 located adjacent the cartridge tip 24 engage the distal tip of the cartridge channel 20 and permit the cartridge 22 to be removably engaged with the cartridge channel 20.

As shown in FIG. 3C, the anvil assembly 30 includes an anvil face 31 located at a distal section of the anvil assembly 30 and an anvil surface or base 33 positioned at a proximal section of the anvil assembly 30. An anvil nose 32 is located adjacent the distal end of the anvil face 31. The anvil assembly 30 also includes an anvil pin hole 37 for receiving an anvil pin 35. The anvil shroud 12 is fit over the anvil assembly 30 at the anvil base 33 and secured thereto.

Referring to FIG. 3B, the cartridge channel assembly 15 also includes an cartridge channel 60 located at the proximal end of the cartridge channel assembly 15 opposite the cartridge channel 20. The cartridge channel 60 and the cartridge channel 20 of the cartridge channel assembly 15 receive a spacer 70. The spacer 70 includes a guide block 72 with a hook latch pivot bore 74 therethrough. The guide block 72 further includes a knife slot 75 and wedge slots 77a and 77b located adjacent the knife slot 75. The spacer 70 also includes spring holes 76 and 78 located near the guide block 72 for receiving a knife locking spring 68 within the holes 76 and 78. The knife locking spring 68 is biased against a knife bar 90. The cutter 10 also includes wedge bars 82 and 84 having a firing wedge 83 and 85 located at the distal end of the wedge bars 82 and 84 respectively. The firing wedges 83 and 85 of the wedge bars 82 and 84 are driven through the wedge slots 77a and 77b of the guide block 72 upon firing of the cutter 10. The proximal ends of the wedge bars 82 and 84 are connected to a knife block 98. The knife bar 90 includes a pusher detent 96 having a bar guide hook 97 at a proximal end of the knife bar 90 which is connected to the knife block 98 and forms a firing and cutting assembly. The knife bar 90 is positioned between the wedge bars 82 and 84 and includes a knife 100a which is a cutting blade or a knife blade at a distal end of the knife bar 90 which is driven through the knife slot 75 parallel to the spacer 70. The knife bar 90 also includes a lock detent 92 and a tab detent 94 located at the distal end of the knife bar 90 adjacent the knife 100a. The knife block 98 is designed to ride along the outer periphery of the wedge bars 82 and 84 as the knife bar 90, which is connected to the knife block 98, is advanced distally upon firing of the cutter 10.

The proximal ends of the wedge bars 82 and 84 are connected to a wedge pusher block 34 which is also located within the cartridge channel 60 of the cartridge channel assembly 15. A cam operator bar 36 which is also a part of the wedge pusher block 34 receives an auditory cam 130. The auditory cam 130 includes a cam hole 139 for receiving a cam pin 137. The cam pin 137 is positioned in cam pin access grooves 65 located in the cartridge channel 60 of the cartridge channel assembly 15 for permitting relative movement of the auditory cam 130 about the cam pin 137.

The cutter 10 is fired by an actuation knob 18 which is manually driven in a distal direction by the user. The actuation knob 18 includes a pusher block attachment hook 19 which is inserted through an actuator slot 62 which is a longitudinal slot in a sidewall of the cartridge channel 60 of the cartridge channel assembly 15. The pusher block attachment hook 19 is connected to the wedge pusher block 34 such that upon manually driving the actuation knob 18 toward the distal end of the cutter 10, the auditory cam 130 is pivoted about the cam pin 137 and the wedge pusher block 34 is driven distally thereby driving the knife block 98 with connected knife bar 90 and wedge bars 82 and 84 through the firing sequence.

The hook latch 50 includes anvil pin fingers 52 at a distal end of the hook latch 50 and a latch hole 56 for receiving a hook latch pivot pin 57 therethrough. The hook latch 50 is secured to the cartridge channel assembly 15 by the alignment of the latch hole 56 with the channel hole 63 in the cartridge channel assembly 15. The hook latch pivot pin 57 is inserted through the latch hole 56 and the channel hole 63.

The hook latch 50 also includes a travel detent 53 on an inner surface of one of the anvil pin fingers 52 and is movably engagable with a travel detent slot 66 located in the cartridge channel assembly 15. The anvil pin fingers 52 also include anvil pin locking slots 54 which are alignable with an anvil pin slot 64 located in the cartridge channel assembly 15.

Upon assembly of the cutter 10 for firing, the anvil pin 35 of the anvil assembly 30 is positioned between and aligned with the anvil pin slot 64 of the cartridge channel assembly 15 such that the cartridge channel 60 receives the anvil base 33 and the anvil face 31 is aligned with and positioned directly opposite the cartridge 22 located in the cartridge channel 20 of the cartridge channel assembly 15.

As shown in FIG. 3A, the hook latch shroud 16 is secured to the hook latch 50 by a locking cleat 46 which is engaged with a cleat slot 51 on the hook latch 50. Thus, upon assembly of the cutter 10, the anvil pin fingers 52 of the hook latch 50 ride against the anvil pin 35 until the anvil pin 35 comes to rest in the anvil pin locking slot 54 and the hook latch 50 is fully seated against the cartridge channel assembly 15 thereby locking the instrument in a closed configuration. This closed configuration permits tissue to be captured between the anvil face 31 and the cartridge 22 for transection.

Once tissue has been selected for fastening and transection, the tissue is placed between the anvil face 31 and the cartridge 22. The cutter 10 is assembled in a closed and locked configuration in the manner mentioned above such that the anvil nose 32 located at the distal end of the anvil face 31 is positioned directly opposite the cartridge tip 24. A tissue gap pin 26 (FIG. 2) is located between the cartridge 22 and the anvil face 31 and ensures proper spacing or tissue gap 28 between the cartridge 22 and the anvil face 31. In order to transect the tissue, the actuation knob 18 is manually driven distally thereby driving the knife bar 90 and wedge bars 82 and 84 in a distal direction and affecting a simultaneous fastening and transecting of the tissue. Accordingly, the staples are driven through pockets 29 and ejected from the cartridge 22 through the tissue to the anvil face 31.

The knife bar 90, as shown in greater detail in FIG. 4, includes the knife 100a (FIG. 5) located at the distal end of the knife bar 90 and having a knife edge 101a at the leading edge of the knife 100a. The knife edge 101a cuts through the tissue as the knife bar 90 is actuated upon firing of the cutter 10 and simultaneously cuts the tissue as the staples are ejected from the cartridge 22.

FIG. 5 illustrates a preferred embodiment of the knife 100a. FIGS. 6 and 7 illustrate alternative embodiments of the knife 100b and 100c respectively. As shown in FIG. 5, the knife edge 101a of the knife 100a is located at the leading edge of the knife 100a and has a wave-shaped serrated blade configuration consisting of a plurality of pairs of cutting tips 102a for piercing the tissue directly and grooves or notches 104a positioned between each cutting tip 102a. Accordingly, each pair of cutting tips 102a has a notch 104a positioned or interposed therebetween.

FIG. 6 illustrates a second embodiment of the knife 100b which includes a knife edge 101b consisting of a scalloped serrated blade configuration comprising a plurality of pairs of cutting tips 102b. A cutting notch 104b located between each pair of cutting tips 102b.

FIG. 7 shows a third embodiment of the knife 100c having a knife edge 101c which consists of a V-shaped serrated blade configuration comprising a plurality of pairs of cutting tips 102c. A notch 104c is located between each pair of cutting tips 102c.

The unique blade configurations of the present invention, as shown in FIGS. 5–7, provide for a novel and efficient cutting action on tissue as well as ensure that the respective cutting edges 101a, 101b and 101c remain sharp and prohibit dulling even after repeated usages. The cutting tips 102a, 102b and 102c are tips which are designed to pierce directly through tissue upon actuation of the cutter 10 as the knife bar 90 is advanced along its cutting stroke.

The serrated blade configuration of the present invention not only provides that the tissue is pierced and transected by cutting tips 102a, 102b and 102c, but also, if any object is encountered, such as a staple, it is trapped or captured directly within one of the respective notches 104a, 104b or 104c in order to prevent the staple from riding along the knife edge 102a, 102b or 102c. Since the object in the transected tissue is captured in one of the notches 104a, 104b or 104c, the knife edge 101a, 101b or 101c will remain relatively sharp and permit subsequent transections with the same cutting knife.

Accordingly, the present invention can be utilized in various types of tissue including tissue that has a foreign object, such as a previously fired staple, and permits an effective transection of the tissue by maintaining a relatively sharp blade edge even after repeated usages.

Although this invention has been described in connection with its most preferred embodiment, it will become readily apparent to those reviewing this detailed specification that numerous additional embodiments fall well within the scope and spirit of the claimed invention as set forth in the claims which appear below.

What is claimed is:

1. A method for fastening and cutting tissue having an object located in the tissue comprising the steps of:

providing a surgical tissue fastening device comprising a handle, a cartridge assembly connected to said handle, said cartridge assembly including a cartridge containing a plurality of surgical fasteners, an anvil assembly connected to said handle and positionable adjacent said cartridge assembly, said anvil assembly including an anvil surface for receiving and for forming said fasteners ejected from said cartridge, said anvil surface and said cartridge adapted for receiving tissue therebetween, a knife blade movable between said cartridge and said anvil surface for cutting said tissue, said knife blade having a knife edge comprising a plurality of pairs of cutting tips and a notch interposed between each pair of cutting tips for capturing an object encountered during movement of said knife blade and an actuator assembly operatively connected to said cartridge assembly and said knife blade for ejecting said fasteners from said cartridge to said anvil surface through said tissue and for advancing said knife blade for cutting said tissue between said cartridge and said anvil surface;

positioning said tissue between said cartridge and said anvil surface;

ejecting said fasteners into said tissue between said cartridge and said anvil surface; and advancing said knife blade through said tissue between said cartridge and said anvil for cutting said tissue with said knife edge wherein said object is encountered and captured in said notch.

2. A method for transecting tissue having an object located in the tissue to be transected comprising the steps of:

providing a surgical tissue fastening device comprising a handle, a cartridge assembly connected to said handle, said cartridge assembly including a cartridge containing a plurality of surgical fasteners, an anvil assembly connected to said handle and positionable adjacent said cartridge assembly, said anvil assembly including an anvil surface for receiving and for forming said fasteners ejected from said cartridge, said anvil surface and said cartridge adapted for receiving tissue therebetween, a knife blade movable between said cartridge and said anvil surface for cutting said tissue, said knife blade having a knife edge comprising a plurality of pairs of cutting tips and a notch interposed between each pair of cutting tips and an actuator assembly operatively connected to said cartridge assembly and said knife blade for ejecting said fasteners from said cartridge to said anvil surface through said tissue and for advancing said knife blade for cutting said tissue between said cartridge and said anvil surface;

positioning said tissue between said cartridge and said anvil surface;

ejecting said fasteners into said tissue between said cartridge and said anvil surface; and advancing said knife blade through said tissue between said cartridge and said anvil for cutting said tissue with said knife edge wherein said object in said tissue is contained within one notch between a pair of cutting tips.

* * * * *